United States Patent [19]

Scheinmann et al.

[11] Patent Number: 6,046,313
[45] Date of Patent: Apr. 4, 2000

[54] PROCESS FOR MAKING MORPHINE-6-GLUCURONIDE OR SUBSTITUTED MORPHINE-6-GLUCURONIDE

[75] Inventors: Feodor Scheinmann, Cheshire; Keith William Lumbard, Stockport; Richard Talbot Brown, Cheadle Hulme; Stephen Patrick Mayalarp; Neil Edward Carter, both of Manchester, all of United Kingdom

[73] Assignee: Salford Ultrafine Chemicals and Research Limited, Manchester, United Kingdom

[21] Appl. No.: 08/688,727

[22] Filed: Jul. 31, 1996

Related U.S. Application Data

[60] Division of application No. 08/192,281, Feb. 4, 1994, Pat. No. 5,621,087, which is a continuation-in-part of application No. PCT/GB92/01449, Aug. 4, 1992.

[30] Foreign Application Priority Data

Aug. 6, 1991 [GB] United Kingdom ............... 9116909

[51] Int. Cl.$^7$ ............... C07D 489/00; C07H 13/02; C07H 1/00; C07G 3/00
[52] U.S. Cl. ............... 536/4.4; 536/119; 536/124; 546/44
[58] Field of Search ............... 536/4.4, 119, 124; 546/44

[56] References Cited

U.S. PATENT DOCUMENTS 4,774,230  9/1988  Tuttle et al. .

FOREIGN PATENT DOCUMENTS

| 0 324 212 A1 | 7/1989 | European Pat. Off. . |
| WO 93/03051 | 2/1993 | WIPO . |
| WO 93/05057 | 3/1993 | WIPO . |
| WO 95/16050 | 6/1995 | WIPO . |

OTHER PUBLICATIONS

"Metabolism of Citalopram in Man", abstract, International Society of Xenobiotics, Oct. 21–25, 1994.
Kaspersen, F.M., and Van Boeckel, C.A.A., "A review of the methods of chemical synthesis of sulphate and glucuronide conjugates", *Xenobiotica*, vol. 17, No. 12, 1451–1471, Dec. 1987.
Vlahov, J., and Snatzke, G., "Uber eine verbesserte Synthese von β–Glucosiduronsaure–Derivaten", *Liebigs Ann. Chem.*, 1983, 570–574.
Sy, W.–W., et al., "Syntheses of 3–O– and 6–O–Propanoyl-morphine—A Reinvestigation and Correction", *Journal of Pharmaceutical Sciences*, vol. 75, No. 8, Aug. 1986, 787–789.
Saferstein, R., et al, "Chemical Ionization Mass Spectrometry of Morphine Derivatives", *Journal of Forensic Sciences*, vol. 24, No. 2, Apr. 1979, 312–316.
Manura, J.J., et al., "The Forensic Identification of Heroin", *Journal of Forensic Sciences*, vol. 23, No. 1, Jan. 1978, 44–56.
Bollenback, G.N., et al, "The Synthesis of Aryl–D–glucopyranosiduronic Acids", *J. American Chemical Society*, 1955, 77, 3310–3315.
Osborne, R., et al., "Analgesic Activity of Morphine–6–Glucuronide", *The Lancet*, 1988, 828.
Carrupt, P–A., et al, "Morphine–6–Glucuronide and Morphine 3–Glucuronide as Molecular Chameleons with Unexpected Lipophilicity", *J. Med. Chem.*, 1991, 34, 1272–1275.
Yoshimura, H., et al., *Chem. Pharm. Bull.*, 1968, 16, 2114.
Drustrup et al. *International Journal of Pharmaceutics*, vol. 71, No. 1,2, issued Apr. 22, 1991, pp. 105–116.

*Primary Examiner*—Gary L. Kunz
*Assistant Examiner*—Everett White
*Attorney, Agent, or Firm*—Hollander Law Firm, P.L.C.

[57] ABSTRACT

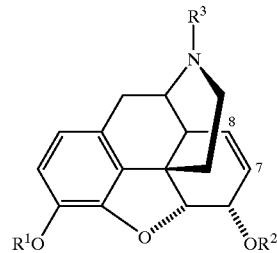

(I)

Morphine-6-glucuronide or substituted morphine-6-glucuronide of formulae (I) is made by conjugation of a glucuronate ester and/or substituted glucuronate ester with morphine or substituted morphine in the presence of a Lewis acid catalyst and in the absence of silver catalysts and barium hydroxide and other heavy metal derivatives.

14 Claims, No Drawings

PROCESS FOR MAKING MORPHINE-6-GLUCURONIDE OR SUBSTITUTED MORPHINE-6-GLUCURONIDE

This application is a division of U.S. Ser. No. 08/192,281, filed Feb. 4, 1994, now U.S. Pat. No. 5,621,087, which is a continuation-in-part of International Application PCT/GB92/01449, with an international filing date of Aug. 4, 1992.

This invention relates to a process for making morphine-6-glucuronide or substituted morphine-6-glucuronide.

Morphine-6-glucuronide (M6G) is a metabolite of morphine in the human body and is a more powerful analgesic than morphine itself (R. Osborne et al., *The Lancet*, 1988, 828 and literature cited therein). It has previously been synthesized by H. Yoshimura et al., (*Chem. Pharm. Bull.*, 1968, 16, 2114) and others e.g. (P-A Carrupt. et al., *J. Med. Chem.*, 1991, 34, 1272) using the Koenigs-Knorr procedure whereby methyl (tri-O-acetyl-D-glucopyranosylbromide) uronate is synthesized (G. N. Bollenback et al., *J. Amer. Chem. Soc.*, 1955, 77, 3310) and reacted with 3-acetylmorphine in the presence of silver carbonate in refluxing benzene. The final isolation of morphine-6-glucuronide requires liberating it from an insoluble barium salt prior to purification by recrystallisation (H. Yoshimura et al *Chem. Pharm. Bull.*, loc. cit. and P-A.Carrupt et al., *J. Med. Chem.*, loc. cit.). Morphine-6-glucuronide is now required in substantial quantities for extensive biological and clinical evaluations. The trace amounts of heavy metals from the Koenigs-Knorr method of production can be very difficult to remove in the final product. Another problem associated with the Koenigs-Knorr reaction is that glycoside formation involves an unstable sugar derivative and a heterogenous reaction system which leads to variable yields of the conjugate and difficulties in purification when the synthesis of morphine-6-glucuronide is carried out on a larger scale.

Similar problems were encountered on producing morphine-3,6-diglucuronide. This compound is also of importance as a metabolite of morphine and its monoglucuronides.

The present invention has been made from a consideration of these problems.

It is the object of the present invention to provide new preparations of morphine-6-glucuronide and morphine-3,6-diglucuronide and their derivatives which use stable intermediates and avoid the Koenigs-Knorr procedure involving the use of heavy metal derivatives e.g. silver and barium reagents in the synthetic process.

According to the present invention there is provided a process for making morphine-6-glucuronide or substituted morphine-6-glucuronide of the following formulae:

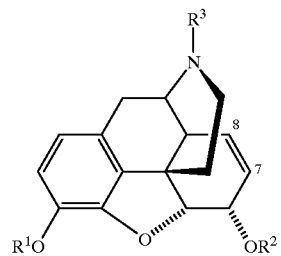

1

Wherein $R^1$, $R^2$ and $R^3$ may be any of the following:
$R^1$=alkyl, aryl, acyl, silyl, phosphate, sulphate, hydrogen or glycoside.
$R^2$=glycoside ester group, acetyl group, β-D-glucuronyl group, or hydrogen.
$R^3$ is alkyl, aryl, hydrogen, alkoxy, aryloxy, halogen, both methyl and →O each attached to the nitrogen of the ring, or $(CH_2)_nX$ where X is $NRR^4$, where n is an integer and R and $R^4$ are hydrogen, alkyl, aryl or acyl, or X is alkoxy, hydroxy, O-acyl, aryloxy or halogen.

Positions 7,8 can be olefin as shown or dihydro-, dihydroxy-, hydroxyhalo-, epoxy-, dihalo-, hydrohalo-, hydrohydroxy-, or CXY (X,Y=halogen or hydrogen) adducts, the method comprising the steps of conjugating a glucuronate ester and/or a substituted glucuronate ester with morphine or substituted morphine using acid catalysis to yield the morphine glucuronate derivative, followed by replacement of $R^1$ (of formula 1) by hydrogen and ester hydrolysis of the glucuronate at $R^2$ (of formula 1).

Preferably $R^1$, $R^2$ and $R^3$ of the morphine-6-glucuronide or substituted morphine-6-glucuronide are present in one of the following combinations:

| $R^1$ | $R^2$ | $R^3$ |
| --- | --- | --- |
| H | β-D-glucuronyl | methyl |
| β-D-glucuronyl | β-D-glucuronyl | methyl |
| acetyl | methyl β-D-(2,3,4-triisobutyryl)glucuronate | methyl |
| benzoyl | methyl β-D-(2,3,4-triisobutyryl)glucuronate | methyl |
| H | methyl β-D-(2,3,4-triisobutyryl)glucuronate | methyl |
| ᵗbutyldimethylsilyl | methyl β-D-(2,3,4-triisobutyryl)glucuronate | methyl |
| isobutyryl | methyl β-D-(2,3,4-triisobutyryl)glucuronate | methyl |
| pivalyl | methyl β-D-(2,3,4-tripivalyl)glucuronate | methyl |
| pivalyl | methyl β-D-(2,3,4-triisobutyryl)glucuronate | methyl |
| methyl β-D-(2,3,4-triacetyl)glucuronate | acetyl | methyl |
| methyl β-D-(2,3,4-triacetyl)glucuronate | methyl β-D-(2,3,4-triacetyl)glucuronate | methyl |
| methyl β-D-(2,3,4-triisobutyryl)glucuronate | methyl β-D-(2,3,4-triisobutyryl)glucuronate | methyl |

-continued

| $R^1$ | $R^2$ | $R^3$ |
|---|---|---|
| methyl | β-D-glucuronyl | methyl |
| H | β-D-glucuronyl | methyl, → O |
| H | β-D-glucuronyl | $(CH_2)_nX$ where X = $NRR^4$, R and R4 being H, alkyl, aryl or acyl; OR or halogen |

The morphine or substituted morphine may comprise the following formula:

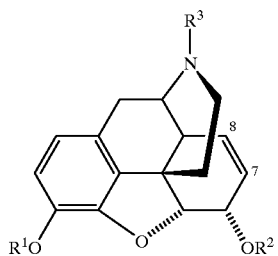

1 wherein
  positions 7,8 can be olefin as shown or dihydro-, dihydroxy-, hydroxyhalo-, epoxy-, dihalo-, hydrohalo-, hydrohydroxy-, or CXY (X,Y=halogen or hydrogen) adducts, and
  wherein $R^1$, $R^2$ and $R^3$ may be any of the following combinations:

| $R^1$ | $R^2$ | $R^3$ |
|---|---|---|
| H | H | methyl |
| acyl | H | alkyl |
| silyl | H | alkyl |
| alkyl | H | alkyl |
| aralkyl | H | alkyl |

The glucuronate esters and substituted glucuronate esters may comprise the following formulae:

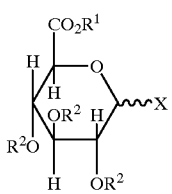

2

Wherein
  $R^1$=alkyl or aryl,
  $R^2$=acyl, silyl, alkyl, benzyl or aryl and
  X=O-acyl, $OC(NH)CCl_3$, $OC(NH)C(halogen)_2R$, hydroxyl, inorganic ester, e.g. phosphate or sulphate derivatives or halogen.

These compounds can be prepared by adapting the procedure given in the specific examples of the present application.

The glucuronate esters and substituted glucuronate esters preferably comprise the following formulae:

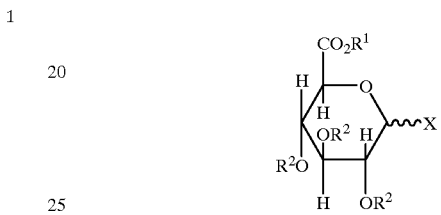

2 wherein $R^1$, $R^2$ and X comprise any of the following:

| $R^1$ | $R^2$ | X |
|---|---|---|
| methyl | acetyl | Br |
| alkyl | acyl | O-acyl |
| alkyl | acyl | OH |
| alkyl | acyl | O—C(NH)—$CCl_3$ |
| methyl | acetyl | α-Cl |
| methyl | acetyl | β-Cl |
| methyl | isobutyryl | β-O-isobutyryl |
| methyl | isobutyryl | α-O-isobutyryl |
| methyl | isobutyryl | OH (α/β) |
| methyl | isobutyryl | α-OH |
| methyl | isobutyryl | α-O—C(NH) $CCl_3$ |
| methyl | isobutyryl | Br (α/β) |
| methyl | pivalyl | β-O-pivalyl |
| methyl | benzoyl | (α/β)-O-benzoyl |

These compounds can be prepared by adapting the procedure given in the specific examples of the present application.

In a preferred embodiment of the present invention the phenolic group of the morphine-6-glucuronide or substituted morphine-6-glucuronide esters is protected. The protected esters may then be isolated. This is followed by alkaline or enzymatic hydrolysis or removal of silyl protecting groups using fluoride for example.

The process of the present invention avoids the use of barium hydroxide and other heavy metals in the synthesis.

This invention uses D-glucurono-6,3-lactone which is converted to esters of tetra-O-acyl-β-D-glucopyranuronates 2 (where the acyl group could include acetyl, propionyl, butyryl, isobutyryl, pivalyl, and other esters of organic acids as well as inorganic esters). The product could then be condensed directly in the presence of a catalyst such as trimethylsilyl triflate or a Lewis acid, with morphine or a derivative whereby the phenolic OH group is protected, e.g. as a silyl, alkyl or aryl ether group or alternatively with an acyl group such as acetyl, benzoyl, isobutyryl, pivalyl and esters of other organic acid as well as inorganic esters. After condensation, protecting groups can be removed by hydrolysis or other selective cleavage. An alternative method of synthesis involves the selective cleavage at position 1 of the ester tetra-O-acyl-β-D-glucopyranuronate (X of formula 2 is O-acyl) to give the corresponding hemiacetal (X is OH) followed by formation of the imidate (X is OC(NH)CCl₃ using for example trichloroacetonitrile in the presence of potassium carbonate or other group I metal carbonates rather than the sodium hydride previously used for such transformations of sugar esters. (R. R. Schmidt, *Angew., Chem.,* Int.Ed. Engl. 1986, 25, 212). Condensation of the imidate in the presence of a Lewis acid, e.g boron trifluoride etherate with either morphine or a suitably protected derivative at position 3 leads to successful glycoside formation. Alternatively the hemiacetal itself can be used or converted to derivatives with other good leaving groups at C-1 for glycoside formation under acid catalysis.

The present invention has been used to produce a large number of new compounds. These compounds include morphine-6-glucuronide derivatives of the following formula:

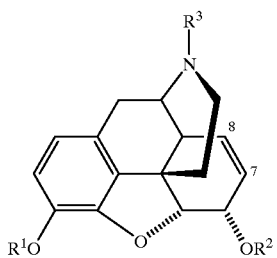

1

Wherein

Positions 7, 8 can be olefin as shown or dihydro-, dihydroxy-, hydroxyhalo-, epoxy-, dihalo-, hydrohalo-, hydrohydroxy-, or CXY (X,Y=halogen or hydrogen), adducts, and Wherein $R^1$, $R^2$ and $R^3$ may be any of the following combinations:

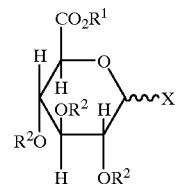

2

Wherein $R^1$, $R^2$ and X may be any of the following combinations:

| $R^1$ | $R^2$ | X |
|---|---|---|
| methyl | isobutyryl | β-isobutyryl |
| methyl | isobutyryl | α-isobutyryl |
| methyl | isobutyryl | OH (α/β) |
| methyl | isobutyryl | α-OH |
| methyl | isobutyryl | α-trichloroacetyl imidoyl |
| methyl | isobutyryl | Br (α/β) |

As specified previously these compounds can be prepared by adapting the procedure given for the specific examples of the present application.

The present invention is described in more detail by way of the following non-limiting examples wherein all parts, percentages and ratios are by weight and all temperatures are in ° C. unless otherwise indicated:

EXAMPLES

Preparation of 3-acetylmorphine (1; $R^1$=Ac, $R^2$=H, $R^3$=Me).

To a stirred suspension of morphine (4 g, 14 mmol) in 10% aqueous sodium bicarbonate (377 ml) was added acetic anhydride (19 ml) over 8.5 minutes. 15 minutes after the addition, ice cold water (300 ml) was added and the solution was extracted with dichloromethane (200 ml). The organic extract was washed with brine, dried over $Na_2SO_4$, and the

| $R^1$ | $R^2$ | $R^3$ |
|---|---|---|
| acetyl | methyl β-D-(2,3,4-triisobutyryl)glucuronate | methyl |
| benzoyl | methyl β-D-(2,3,4-triisobutyryl)glucuronate | methyl |
| H | methyl β-D-(2,3,4-triisobutyryl)glucuronate | methyl |
| ᵗbutyldimethylsilyl | methyl β-D-(2,3,4-triisobutyryl)glucuronate | methyl |
| isobutyryl | methyl β-D-(2,3,4-triisobutyryl)glucuronate | methyl |
| pivalyl | methyl β-D-(2,3,4-tripivalyl)glucuronate | methyl |
| pivalyl | methyl β-D-(2,3,4-triisobutyryl)glucuronate | methyl |
| methyl β-D-(2,3,4-triacetyl)glucuronate | acetyl | methyl |
| methyl β-D-(2,3,4-triisobutyryl)glucuronate | H | methyl |
| methyl β-D-(2,3,4-triacetyl)glucuronate | methyl β-D-(2,3,4-triacetyl)glucuronate | methyl |
| methyl β-D-(2,3,4-triisobutyryl)glucuronate | methyl β-D-(2,3,4-triisobutyryl)glucuronate | methyl |
| isobutyryl | H | methyl |
| pivalyl | H | methyl |
| H | β-D-glucuronyl | methyl, → O |
| H | β-D-glucuronyl | $(CH_2)_nX$ where X = $NRR^4$, R and R4 being H, alkyl, aryl or acyl; OR or halogen |

The process of the invention has also utilized a large number of new sugars of the following formulae:

solvent removed in vacuo to leave a sticky white residue. Trituration with ether gave 3-acetylmorphine (3.68 g, 80%).

The corresponding 3-pivalyl, 3-isobutyryl, 3-propionyl and other 3-acyl derivatives of morphine were also prepared.

Preparation of 3-tert-butyldimethylsilylmorphine (TBDMS-morphine)

To a stirred suspension of anhydrous morphine (7.01 mmol) at −78° C. in anhydrous THF (15 ml) was added 1.6M butyllithium (4.8 ml, 0.492 g, 7.68 mmol) over 8 minutes. 42 minutes later, a solution of TBDMS chloride (1.27 g, 8.43 mmol) in anhydrous THF (10 ml) was added over 10 minutes. The mixture was left to warm up gradually to room temperature overnight by which time all the material had gone into solution. Water was then added to the mixture which was extracted with dichloromethane several times. The organic extracts were combined, washed with brine, dried over $Na_2SO_4$, filtered and the solvent removed in vacuo to leave an off-white film. Chromatography over silica using $CH_2Cl_2$/MeOH (5:1) as eluent afforded the product as a white solid (1.58 g, 56%). Recrystallization from $Et_2O$/petrol (boiling point 40–60°) gave white crystalline needles (1.37 g), m.p.=120–122° C.

Preparation of methyl 1,2,3,4-tetra-O-pivalylglucuronate.

To a suspension of glucuronolactone (10 g, 57 mmol) in MeOH (53 ml) was added NaOMe powder (13 mg). The mixture was left to stir overnight by which time all material had gone into solution. The solvent was removed in vacuo to leave a brown residue, which was dissolved in pyridine (34 ml) and dichloromethane (35 ml) and then cooled to 0° C. Pivalyl chloride (63 ml, 61.66 g, 0.5 mmol) was then added over 2 hours keeping the reaction temperature below 15° C. The mixture was allowed to warm up gradually to room temperature overnight. More dichloromethane was then added, the mixture was washed with 1M HCl (5×40 ml), sodium bicarbonate (5×50 ml), and brine before drying over $Na_2SO_4$, filtering and evaporating to leave a pale colored residue. Addition of petrol (boiling point 40–60°) and subsequent cooling in the refrigerator afforded a white solid which was filtered, washed with more petrol (boiling point 40–60°) and dried in a vacuum oven at 40° C. (25 mm Hg) to give the product (9.66 g, 32%) as white crystals, m.p. 149° C. The corresponding isobutyrate was made by an analogous procedure.

Preparation of methyl 2,3,4-tri-O-acetylglucuronate (2, $R^1$=Me, $R^2$=Ac, X=OH).

Ammonia gas pre-dried by passing it through a bed of sodium hydroxide was bubbled through dichloromethane (200 ml) at −4° C. over 1 hour at a rate which kept the temperature below 0° C. The sugar acetate ($R^1$=Me, $R^2$=Ac, X=OAc) (6 g, 16 mmol) was added to this solution which was stirred at 0° C. for 3.5 hours and then left to stand at room temperature. After 6 hours nitrogen gas was bubbled through the yellow solution for 5 minutes and the mixture left to stand for a further 9.5 hours. By this time some brown gummy material had been deposited and t.l.c. on silica (1:1, petrol (boiling point 40–60°)/EtOAc) indicated that no starting material was left. Nitrogen gas was then bubbled through the solution for 20 minutes and the solution was extracted with ice-cold 10% aqueous hydrochloric acid, then water. After the two phases had been separated, the organic layer was dried ($Na_2SO_4$), filtered and the solvent removed in vacuo to leave the crude product (3.83 g) as a white foam. This product is a mixture of α and β anomers which can be crystallized from chloroform/petrol (boiling point 40–60°). TLC: Rf=0.3 (1.1 petrol (boiling point 40–60°)/EtOAc).IR: 3670-3120, 2940, 1710, 1440 $cm^{-1}$.

The corresponding isobutyrate was made in a similar way.

Preparation of methyl 2,3,4-tri-O-acetyl-1-O-(trichloroacetimidoyl)-α-D-glucuronate (2; $R^1$=Me, $R^2$=Ac, X=OC(NH)$CCl_3$)

To a solution of the preceding hemiacetal (2.8 g, 8.4 mmol) in dichloromethane (30 ml) at room temperature was added trichloroacetonitrile (4.4 ml, 6.39 g, 43.9 mmol) and the solution stirred for 10 minutes. Potassium carbonate was then added and within minutes the mixture started to get darker. After 30 hours it was filtered through a short pad of silica, eluting with ether. The filtrate was concentrated in vacuo to afford the crude product as a sticky pale yellow solid (3.7 g, 93%) which was recrystallized from isopropanol as white crystals (3.1 g). m.p.=107–108°

TLC: Rf=0.52 (1:1 petrol (boiling point 40–60°)/EtOAc); IR: 3320, 2980, 1720, 1680 $cm^{-1}$; δ ($CDCl_3$: 8.76 (1H, bs, HN); 6.63 (1H, d, J=3.5 Hz, 1-H); 5.63 (1H, t, J=9.7 Hz, 4-H); 5.27 (1H, t, J=9.7 Hz, 3-H);5.15 (1H, dd, J=3.5, 9.7 Hz, 2-H); 4.49 (1H, d, J=9.7 Hz, 5-H);3.75 (3H, s, $CO_2$Me); 2.05 (6H, s, Ac); 2.03 (3H, s, Ac).

The corresponding isobutyrate was made in a similar way.

Preparation of methyl 3-acetylmorphine-6-(2'3'4'-triisobutyryl) glucuronate. isobutyryl) glucuronate.

3-Acetylmorphine (0.372 g, 1.14 mmol) dried by azeotroping with benzene was dissolved in dry dichloromethane (4 ml), the tri-isobutyryl imidate (2; X=OC(NH)$CCl_3$, $R^1$=Me, $R^2$=COPr$^i$) (1.28 g, 2.28 mmol) and $BF_3.Et_2O$ (28 μl, 0.0323 g, 2.28 mmol) and 4A molecular sieves added. After stirring at room temperature overnight the mixture was diluted with dichloromethane, washed with sodium bicarbonate, water and brine, dried over $Na_2SO_4$ and the solvent removed in vacuo to leave a pale brown residue (1.53 g). This was chromatographed over silica (40 g) using $CHCl_3$/MeOH (40:1 to 9:1) as eluent to afford the product (0.52 g, 63%) which can be recrystallized from absolute EtOH as off-white crystals, m.p.=188–189° C.

Preparation of morphine-6-glucuronide.

To a solution of the above glucuronate in MeOH (24 ml) was added 5% aqueous NaOH (6 ml) and the mixture was left to stir for 20 hours. T.l.c (n-BuOH/acetone/AcOH/5% aq.$NH_3$/water 45:15:10:10:20) showed that there were two components one of which was M6G and the other morphine. The solution was transferred to a beaker and was acidified with glacial acetic acid (7 ml) which took the pH of the mixture to 5.5. Shortly after this pH was reached (5 minutes), a white solid started to precipitate. The suspension was stirred for a further 30 minutes, the solid filtered and washed with MeOH, and morphine-6-glucuronide (0.4 g, 52%) was obtained after drying at 120° C. for 4 hours, m.p. 240–243° C. More M6G could be obtained by cooling the filtrate.

Preparation of dimethyl morphine-3,6-di(2,3,4-triisobutyryl)glucuronate.

To a stirred suspension of morphine 7.02 mmol), the triisobutyryl imidate (2) ($R^1$=Me, $R^2$=COPr$^i$, X=OC(NH)$CCl_3$) (15.79 g, 28.08 mml) and 4A molecular sieves in dichloromethane (40 ml) at room temperature under argon was added $BF_3.Et_2O$ (3.53 ml, 3.98 g, 28.08 mmol) After only 15 minutes virtually all of the starting material had gone into solution, which was left to stir for 2 days. The solution was diluted with dichloromethane, washed with sodium bicarbonate, water, brine and dried over $Na_2SO_4$. Filtration and evaporation afforded reddish brown gummy crystals. Chromatography over silica (225 g) using $CHCl_3$/MeOH (40:1–9:1) as eluent gave crude diglucuronate which was crystallized by trituration with EtOH. After filtration and drying the dimethyl morphine-3,6-di(2,3,4-triisobutyryl) glucuronate (4.3 g), m.p.229–230°, was obtained. The filtrate was cooled in a refrigerator to afford a second crop of product (277 mg).

C, H, N analysis: Found: C, 60.6; H, 6.9; N, 1.3 $C_{55}H_{75}NO_{21}$ requires C, 60.8; H, 6.9; N, 1.3.

Preparation of morphine-3,6-diglucuronide.

To a stirred suspension of the above dimethyl morphine-3,6-diglucuronate (2 g, 1.84 mmol) in MeOH (60 ml) was added 5% aqueous NaOH (10.3 ml). Most of the solid went into solution after 15 minutes and the mixture was left to stir overnight. The clear solution was then acidified with glacial acetic acid to pH6 and the resulting precipitate was filtered and washed with MeOH. Drying at 60° under high vacuum gave crude morphine-3,6-diglucuronide (0.92 g) which was recrystallized from hot water/MeOH, m.p. 243–244° (dec.)

It is to be understood that the above described examples are by way of illustration only. Many modifications and variations are possible.

We claim:

1. A compound selected from the following formulae:

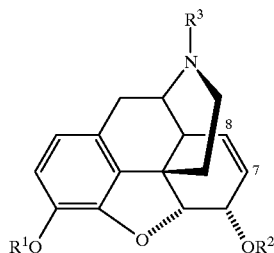

wherein positions 7, 8 is olefin as shown or dihydro-, dihydroxy-, hydroxyhalo-, epoxy-, dihalo-, hydrohalo-, or hydrohydroxy-, adducts, and wherein $R^1$, $R^2$, and $R^3$ are one of the combinations selected from the group consisting of combinations:
a) $R^1$ is methyl β-D-(2,3,4-triacetyl)glucuronate, $R^2$ is acetyl, and $R^3$ is methyl,
b) $R^1$ is methyl β-D-(2,3,4-triisobutyryl)glucuronate, $R^2$ is hydrogen, and $R^3$ is methyl, and
c) $R^1$ is pivalyl, $R^2$ is hydrogen, and $R^3$ is methyl.

2. A compound as claimed in claim 1 wherein $R^1$ is methyl β-D-(2,3,4-triacetyl)glucuronate, $R^2$ is hydrogen, and $R^3$ is methyl.

3. A compound as claimed in claim 1 wherein $R^1$ is methyl β-D-(2,3,4-triisobutyryl)glucuronate, $R^2$ is hydrogen, and $R^3$ is methyl.

4. A compound as claimed in claim 1 wherein $R^1$ is pivalyl, $R^2$ is hydrogen, and $R^3$ is methyl.

5. A compound selected from the following formulae:

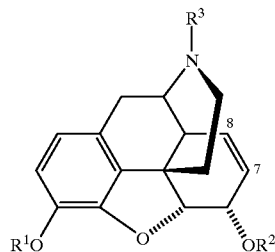

wherein positions 7, 8 is dihydro-, dihydroxy-, hydroxyhalo-, epoxy-, dihalo-, hydrohalo-, or hydrohydroxy-, adducts, and wherein $R^1$, $R^2$, and $R^3$ are one of the combinations selected from the group consisting of combinations:
a) $R^1$ is isobutyryl, $R^2$ is hydrogen, and $R^3$ is methyl, and
b) $R^1$ is pivalyl, $R^2$ is hydrogen, and $R^3$ is methyl.

6. A compound as claimed in claim 5 wherein $R^1$ is isobutyryl, $R^2$ is hydrogen, and $R^3$ is methyl.

7. A compound as claimed in claim 5 wherein $R^1$ is pivalyl, $R^2$ is hydrogen, and $R^3$ is methyl.

8. A compound selected from the following formulae:

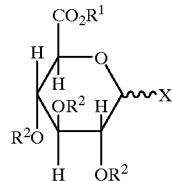

wherein $R^1$, $R^2$ and X are one of the combinations selected from the group consisting of combinations:
a) $R^1$ is methyl, $R^2$ is isobutyryl, and X is β—O-isobutyryl,
b) $R^1$ is methyl, $R^2$ is isobutyryl, and X is α—O-isobutyryl,
c) $R^1$ is methyl, $R^2$ is isobutyryl, and X is OH (α/β),
d) $R^1$ is methyl, $R^2$ is isobutyryl, and X is α—OH,
e) $R^1$ is methyl, $R^2$ is isobutyryl, and X is α—O—C(NH)CCl$_3$, and
f) $R^1$ is methyl, $R^2$ is isobutyryl, and X is Br (α/β).

9. A compound as claimed in claim 8 wherein $R^1$ is methyl, $R^2$ is isobutyryl, and X is β—O-isobutyryl.

10. A compound as claimed in claim 8 wherein $R^1$ is methyl, $R^2$ is isobutyryl, and X is α—O-isobutyryl.

11. A compound as claimed in claim 8 wherein $R^1$ is methyl, $R^2$ is isobutyryl, and X is OH (α/β).

12. A compound as claimed in claim 8 wherein $R^1$ is methyl, $R^2$ is isobutyryl, and X is α—OH.

13. A compound as claimed in claim 8 wherein $R^1$ is methyl, $R^2$ is isobutyryl, and X is α—O—C(NH)CCl$_3$.

14. A compound as claimed in claim 8 wherein $R^1$ is methyl, $R^2$ is isobutyryl, and X is Br (α/β).

* * * * *